United States Patent
Diawara et al.

(10) Patent No.: US 7,639,783 B1
(45) Date of Patent: Dec. 29, 2009

(54) PARALLAX FREE AND SPARK PROTECTED X-RAY DETECTOR

(75) Inventors: Yacouba Diawara, Madison, WI (US); Bruce L. Becker, Madison, WI (US); Roger D. Durst, Middleton, WI (US); Menyhert Kocsis, Venon (FR)

(73) Assignee: Bruker AXS, Inc., Madison, WI (US)

( * ) Notice: Subject to any disclaimer, the term of this patent is extended or adjusted under 35 U.S.C. 154(b) by 0 days.

(21) Appl. No.: 12/131,341

(22) Filed: Jun. 2, 2008

(51) Int. Cl.
 *H05G 1/64* (2006.01)
 *G01N 23/20* (2006.01)

(52) U.S. Cl. .......................... 378/98.8; 378/71

(58) Field of Classification Search .............. 378/19, 378/98.8; 250/374, 397
See application file for complete search history.

(56) References Cited

U.S. PATENT DOCUMENTS

| | | | |
|---|---|---|---|
| 4,317,038 A | 2/1982 | Charpak | |
| 4,595,834 A | 6/1986 | Burns | |
| 4,954,710 A | 9/1990 | Comparat et al. | |
| 5,521,956 A | 5/1996 | Charpak | |
| 6,011,265 A * | 1/2000 | Sauli | 250/374 |
| 6,340,819 B1 * | 1/2002 | Durst et al. | 250/374 |

OTHER PUBLICATIONS

Zanevsky, Yu.V., et al., "Parallax-Free X-Ray Area Detector With High Spatial Resolution", Nuclear Physics B (Proc. Suppl.), 44 (1995), pp. 406-408.

Berskin, A., et al., "A Multistep Parallax-Free X-Ray Imaging Counter", Nuclear Instruments and Methods, 195, (1982), pp. 469-473, North-Holland Publishing Company.

"Hi-Star Area Detector" Bruker Advanced X-Ray Solutions, Bruker AXS, (2001).

Charpak, G., "Parallax-Free, High-Accuracy Gaseous Detectors For X-Ray and VUV Localization", Nuclear Instruments and Methods, 201, (1982), pp. 181-192, North-Holland Publishing Company.

Charpak, G., et al., "The Spherical Drift Chamber For X-Ray Imaging Applications", Nuclear Instruments and Methods, 122, (1974), pp. 307-312, North-Holland Publishing Company.

Kahn, R., et al., "An Area-Detector Diffractometer For the Collection of High Resolution and Multiwavelength Anomalous Diffraction Data in Macromolecular Crystallography", Nuclear Instruments and Methods, 201, (1982), pp. 181-192, North-Holland Publishing Company.

(Continued)

*Primary Examiner*—Irakli Kiknadze
(74) *Attorney, Agent, or Firm*—Law Offices of Paul E. Kudirka

(57) ABSTRACT

An X-ray detector is formed with a geometry in the form of a spherical polygon, including an entrance window, a grid and an anode. The spherical polygonal entrance window and the grid form a spherical polygonal drift region between them. The electric field in this region is radial and eliminates parallax broadening. A spherical polygonal amplification region between a resistive anode on an insulating support and the grid allows very high gas amplification and good protection against spark discharges. A readout electrode on the back side of the anode insulator detects induced charges and protects the readout electronics against sparks.

10 Claims, 3 Drawing Sheets

OTHER PUBLICATIONS

Khazins, D.M., et al., "A Parallel-Plate Resistive-Anode Gaseous Detector for X-Ray Imaging", IEEE Transactions on Nuclear Science, vol. 51, No. 3, Jun. 2004, pp. 943-947.

Rehak, P., et al., "A Method for Reduction of Parallax Broadening in Gas-Based Position Sensitive Detectors", IEEE Transactions on Nuclear Science, vol. 44, No. 3, Jun. 1997, pp. 651-655.

Van Esch, P., et al. "An Electrostatic Lens to Reduce Parallax in Gas Detectors With Cylindrical Geometry", Nuclear Instruments and Methods in Physics Research A 540 (2005) pp. 361-367.

Zanevsky, Yu.V., et al., "Test Results of the Parallax-Free X-Ray Area Detector SD-1000 in the Diffractometer CARD-7", Nuclear Instruments and Methods in Physics A 367 (1995), pp. 76-78.

* cited by examiner

PARALLAX FREE AND SPARK PROTECTED X-RAY DETECTOR

BACKGROUND

Gaseous detectors for detecting ionizing radiation are well-known. FIG. 1 shows a schematic diagram of such a gaseous detector having a planar geometry. X-rays 122 entering the detector pass through an X-ray transparent cathode or window 112 and enter a drift region 118 located between cathode 112 and a mesh layer 124. The drift region 118 is filled with a material that is typically a working gas, such as a quenched noble gas mixture that absorbs X-rays. When an X-ray is absorbed in the working gas, fast photoelectrons are produced along the X-ray trajectory. Secondary electrons 125 issued from the thermalization of the photoelectrons accelerate in the drift region 118 in response to an electric potential provided by voltage source 116. The electrical potential in region 118 is selected so that it is not high enough to induce electron avalanche multiplication. After passing through the mesh 124, the electrons enter a high field amplification region between mesh 124 and resistive anode 128. The electric potential in this region is provided by voltage source 117, which produces an electric potential than is higher than that produced by voltage source 116. The electric potential in amplification region 119 is selected so that the field strength in that region is sufficient to induce electron avalanche multiplication within the working gas.

The electron avalanche phenomenon within the gas results in the formation of an electron cloud 126 that that is absorbed by the anode 128. Anode 128 is typically a layer that has no defined conductive paths, but which is a reasonably homogeneous material of predetermined resistivity. As shown in FIG. 1, the anode is connected to ground at the edges, so the electrical energy absorbed from the electron cloud eventually dissipates. However, the anode material is resistive enough that there is a temporary accumulation of electric charge in the local region of the anode 128 upon which the electron cloud is incident.

Positioned adjacent to the anode 128 to the side opposite to the incoming electron cloud is a readout structure 130 which is conventionally comprised of two orthogonal serpentine delay lines strips or pixels. As the electron cloud encounters the resistive anode 128, the deposited charge creates a capacitive coupling between the anode and the delay lines of the readout structure 130. This capacitive coupling induces currents in certain paths of the delay lines of the readout structure 130. These currents are detected by detection circuit 115, and have a temporal signature indicative of the parallel paths in which they were induced. This temporal signature may be used to determine the position of the electron cloud in the detection plane.

Gaseous detectors of this type have a number of very attractive features for imaging ionizing radiation including a large active area, low noise and high count rate capability. However, they typically require the radiation to pass through at least a centimeter thickness of gas in drift region 118 in order to achieve good detection efficiency. The thickness of region 118, in turn, introduces a non-desirable parallax error in the output.

The parallax error of a planar geometry gaseous detector, such as that shown in FIG. 1, is fundamentally limited by the detector geometry and the electric field in the drift region 118. In particular, the secondary electrons 125 will drift along the electric field lines emerging from the cathode 112. Parallax broadening occurs if the field lines do not coincide with the original X-ray photon direction. This is illustrated in FIG. 1 where an X-ray 140 strikes the detector at an oblique angle. As mentioned above, when the X-ray is absorbed in the working gas, fast photoelectrons are produced along the X-ray trajectory. However, because the X-ray travels at an angle with respect to the electric field lines, these photoelectrons are produced at different positions along the length of the detector. Secondary electrons 145 and 155 issued from the thermalization of these photoelectrons accelerate in the drift region 118 and produce avalanches 150 and 160 in the amplification region 119. The result is an asymmetric broadening of the diffraction spots. This undesirable effect becomes more pronounced at higher angles of incidence. To eliminate the parallax, the electric field lines along which secondary electrons move must emanate from a focal point which coincides with the position of the sample under study.

Some prior art attempts to overcome this problem have used a spherical conversion volume generated by a proportional wire chamber equipped with a resistive divider adapted to generate appropriate spherical equipotential surfaces within the drift space of the wire chamber.

Other conventional approaches use a radially symmetric change of the potential (spherical field) in the entrance window to the detector or in the cathode. For example, such a spherical field can be created by using a curved entrance window at constant potential. The problem with this approach is that the thickness of the conversion region changes considerably in the z direction, which is acceptable only for certain applications. In addition, a parallax error is still observed in these structures.

Replacing the parallel drift field with a radial drift field has been used in other prior art approaches. In these approaches, the parallax error is reduced, but only on a limited sensitive area of the detector, mainly near the central region.

In still another approach, the detector structure is based on a spherical gas electron multiplier, which serves as a transfer electrode with limited amplification to compensate for transparency losses.

SUMMARY

In accordance with the principles of the invention, an X-ray detector is formed with a geometry in the form of a spherical polygon, including an entrance window, a grid and an anode. The spherical polygonal entrance window and the grid form a spherical polygonal drift region between them. The electric field in this region is radial and eliminates parallax broadening. A spherical polygonal amplification region between a resistive anode on an insulating support and the grid allows very high gas amplification and good protection against spark discharges. A spherical readout electrode on the back side of the anode insulator detects induced charges and protects the readout electronics against sparks.

DETAILED DESCRIPTION

Figure 2:
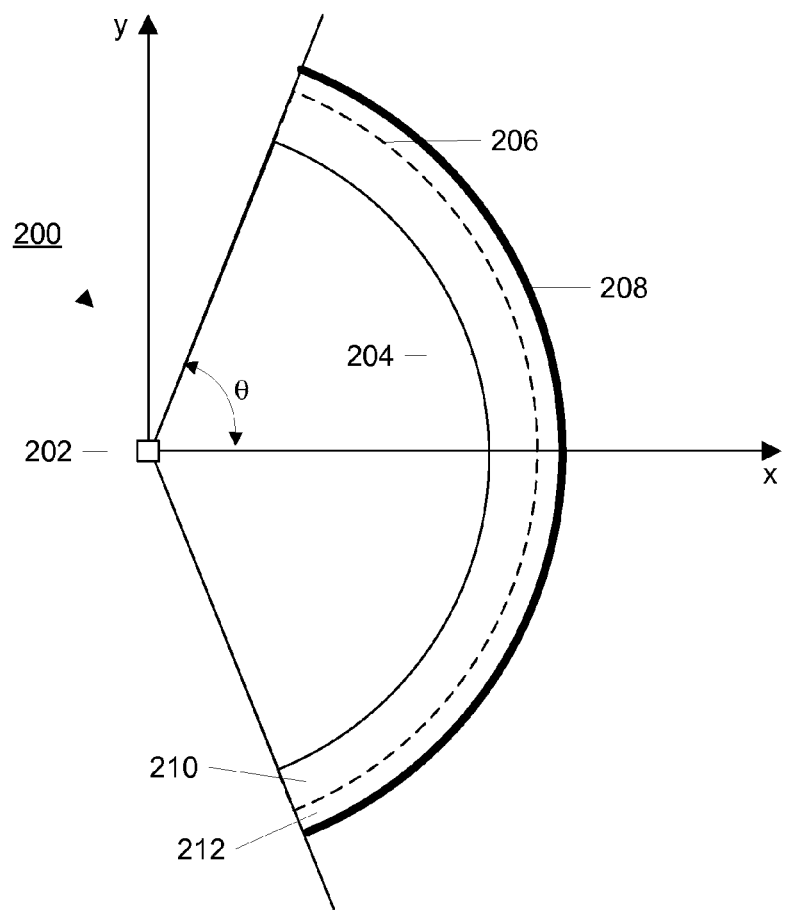
FIG. 2 is a schematic cross section of an X-ray detector constructed in accordance with the principles of the current invention.

FIG. 2 shows a cross section of an X-ray detector 200 constructed in accordance with the principles of the present invention. The detector 200 comprises a cathode or entrance window 204 which is fabricated from a material that is substantially transparent to X-rays, such as beryllium, in the shape of a spherical polygon. A grid 206, also in the shape of a spherical polygon, is positioned concentrically with the entrance window 204. The entrance window 204 and the grid 206 form a drift region 210 in the form of the spherical polygon. A potential applied to the entrance window 204 causes the electric field lines at the entrance window (not shown in FIG. 2) to radially point to a sample in a sample holder at position 202. The acceleration region 212 is defined by the grid 206 and the readout structure 208 also in the shape of a spherical polygon. The readout structure 208 is shown in more detail in FIG. 3 and discussed below. The spherical polygonal shape of the detector can cover a large spherical angular range 20 from 7 to ~27 (180°-~360°) which is ideal for diffraction pattern measurements.

When an X-ray is absorbed in the spherical drift region 210 of the detector a fast photoelectron is produced. In the energy range of interest, this fast electron travels perpendicularly the radial field while producing secondary ionization in the form of electron-positive ion pairs. The range of this fast electron sets the physical limit of the spatial resolution of the detector, which is typically of order several tens of microns at high pressure. This parallax free structure can have large drift volume and be used therefore for a good efficiency even at high x-ray energies.

Figure 3:
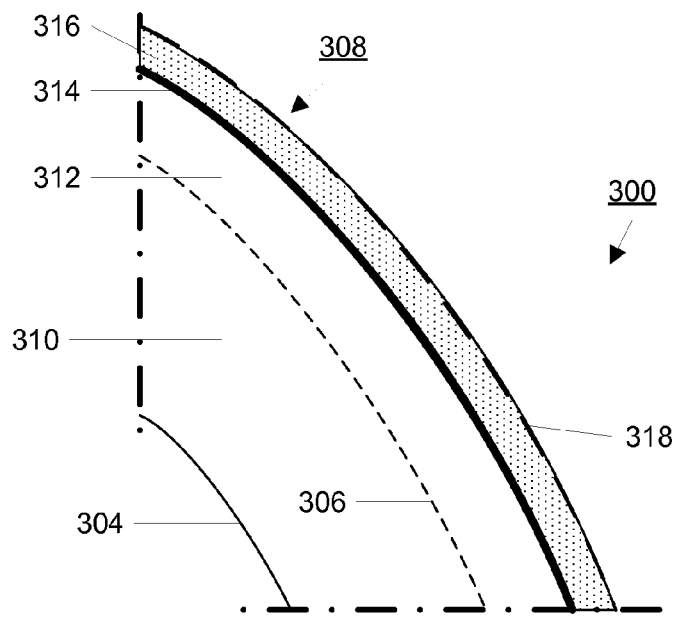
FIG. 3 is an enlarged section of the X-ray detector shown in FIG. 2.

FIG. 3 shows an enlarged view of a portion 300 of the anode and electrical readout structure. In the Figure, elements that correspond to those in FIG. 2 have been given corresponding numeral designations. For example, entrance window 204 in FIG. 2 corresponds to entrance window 304 in FIG. 3. The entrance window 303 and the grid 306 form a drift region 310 as discussed above. An acceleration region 312 is formed between the grid 306 and a readout structure 308. The readout structure comprises a resistive anode 314 formed on an insulating substrate 316, for example, a ceramic substrate. A readout electrode structure 318 is formed on the opposite side of the insulating substrate 316.

The anode 314 is a resistive layer that has no defined conductive paths, but which is a reasonably homogeneous material of predetermined resistivity. The anode is connected to ground at the edges, so that electrical energy absorbed from the electron avalanche cloud eventually dissipates. However, the anode material is resistive enough that there is a time delay for the dissipation. That is, there is a temporary accumulation of electric charge in the local region of the anode 314 upon which an electron avalanche cloud is incident. Positioned on the opposite side of the insulating substrate 316 that supports the resistive anode 314 is a readout electrode structure 318 which comprises two orthogonal serpentine delay lines. As the electron avalanche cloud encounters the resistive anode 314, the deposited charge creates a capacitive coupling between the anode and the delay lines of the readout electrode structure 318 through the insulating substrate 316. This capacitive coupling induces currents in certain paths of the delay lines of the readout structure 318. These currents are detected by a detection circuit (not shown in FIG. 3) and have a temporal signature indicative of the parallel paths in which they were induced. Thus, the capacitively-induced charges may be used to determine the position of the electron cloud in the detection sphere. The readout arrangement is described in more detail in U.S. Pat. No. 6,340,819, which is incorporated in its entirety by reference.

Figure 1:
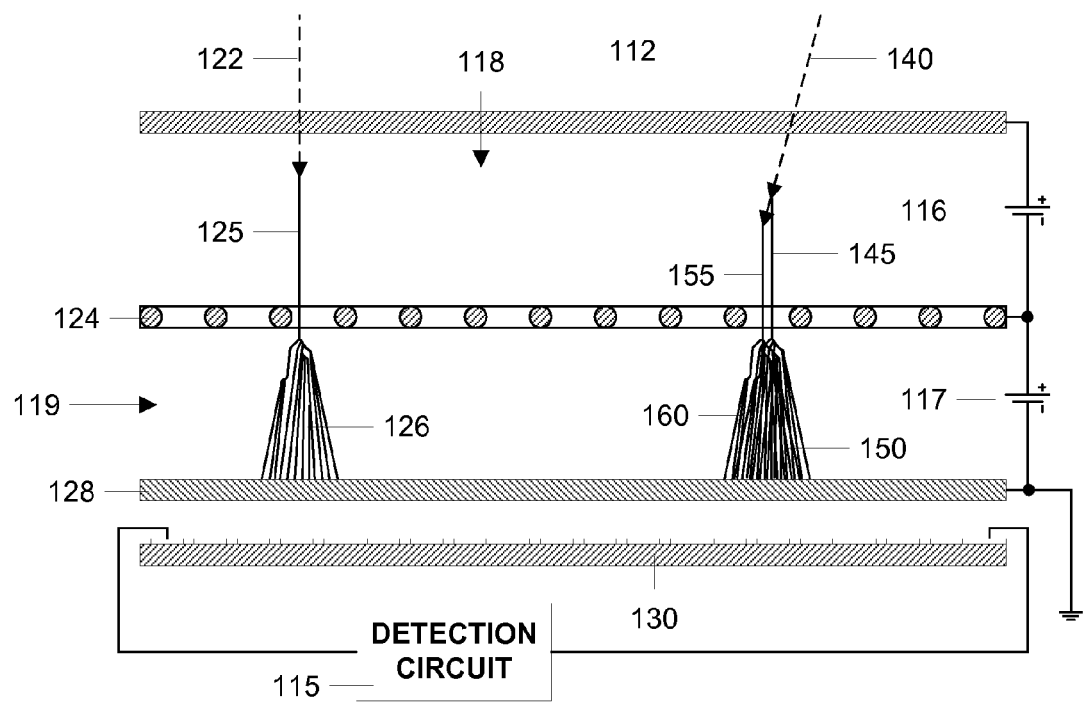
FIG. 1 is a block schematic diagram of the conventional parallel plate gaseous detector for ionizing radiation.

The inventive spherical configuration offers several unique improvements over conventional designs. In particular, for a conventional parallel plate gaseous detector, such as that shown in FIG. 1, the maximal and the average electric field strength (E) in the amplification region are equal and defined by the potential difference divided by the electrode separation:

$$E_{MAX} = \frac{V}{x}$$

where V is the voltage applied the amplification region and x is the distance between the grid and the anode. The electric field strength is uniform in the gap between the grid and the anode. A so-called field enhancement factor can be defined as the maximum electric field divided by the average electric field. A field enhancement factor of 1.0 therefore represents no enhancement over the average field.

In the inventive structure, for two concentric spherical electrodes, the maximal electric field is given by the following equation:

$$E_{MAX} = \frac{V}{(b-a)} \frac{b}{a}$$

where V is the voltage applied between the spherical electrodes, a is the radius of the inner spherical electrode and b is the radius of the outer spherical electrode.

Figure 4:
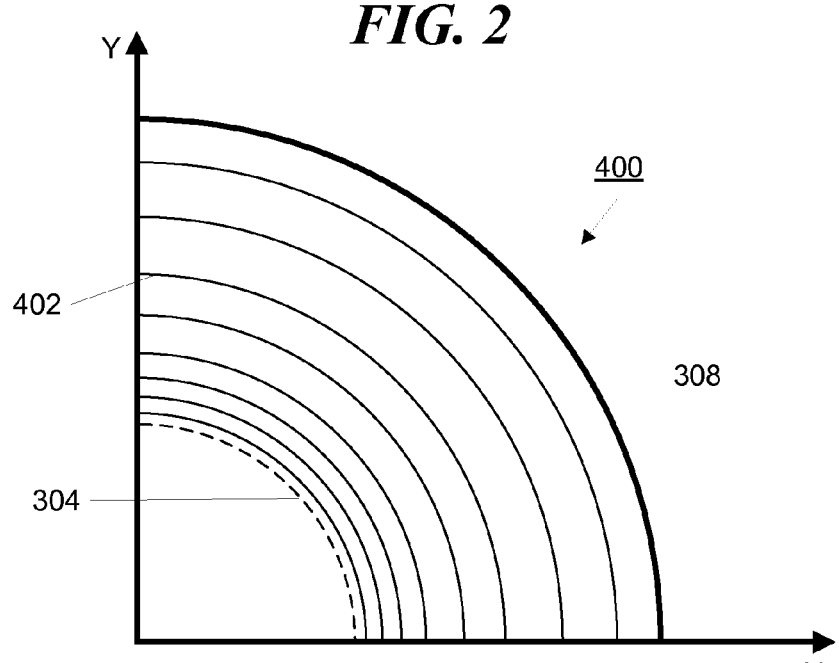
FIG. 4 is a graph of field strength in a quadrant of the amplification region of the inventive detector structure.

In the case of a spherical amplification structure, like that provided in the inventive structure, the inner spherical electrode corresponds to the grid and the outer spherical electrode corresponds to the anode. This structure provides a field enhancement factor (b/a) which is larger than 1.0. FIG. 4 shows a plot 400 of the field strength in one quadrant of a spherical amplification structure. The lines, such as line 402, represent equipotential surfaces and the spacing of the lines indicates field strength. As shown in the figure, field strength increases from the resistive anode 308 towards the grid 304.

This field enhancement offers several advantages. For example, unlike the conventional parallel plate avalanche counter where there is no field enhancement, the inventive detector can be operated at a smaller voltage compared to the conventional design, thereby increasing the detector stability.

Further, the amplitude of the electric field increases in the direction toward the grid. This non-uniformity of the field inhibits the formation of electrical streamers, and therefore spark propagation, from the anode.

In addition, due to a higher field strength close to the grid, the majority of the electron avalanche multiplication takes place near the grid. Therefore, most of the avalanche signal is created close to the grid surface, which reduces the rise-time of the electronic signal.

Another benefit is that most of the positive ions that are created during the secondary ionization are created close to the grid to which they are attracted and cleared by collision with the grid. Consequently, they do not have to drift across the entire acceleration region and are cleared more rapidly. Therefore, the so-called "space-charge effect" is less pronounced than in conventional detectors and the local countrate capability of the inventive detector is increased.

Figure 5:
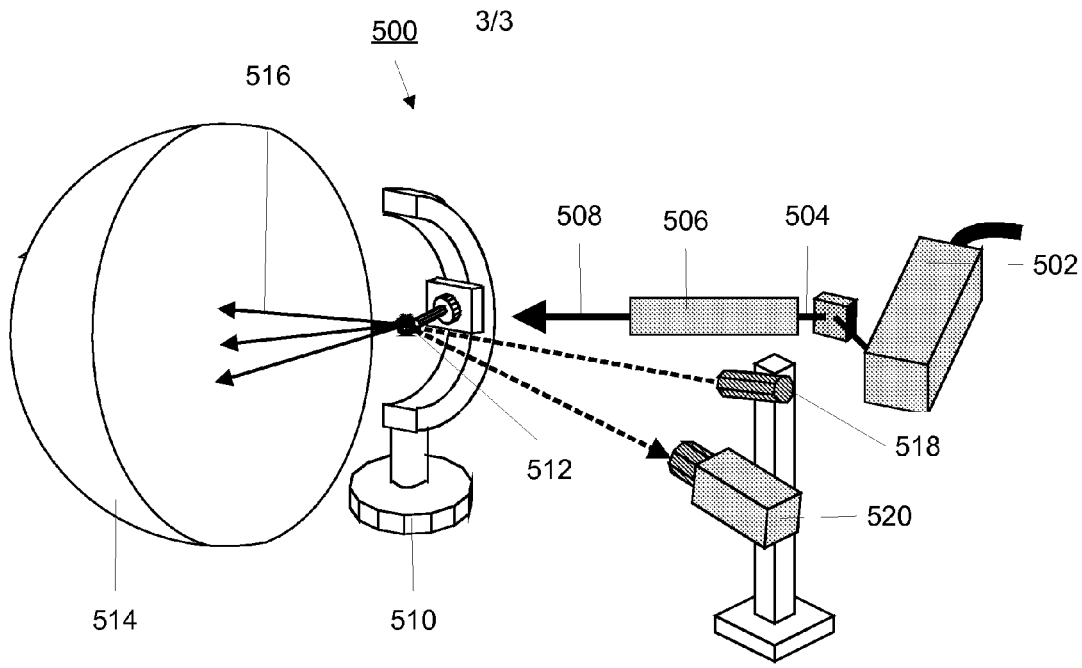
FIG. 5 is an X-ray diffraction system employing the detector shown in FIGS. 2 and 3.

FIG. 5 shows a typical laboratory X-ray diffraction system 500 for performing single crystal diffraction experiments. The system 500 includes an X-ray source 502 that produces a primary X-ray beam 504 with the required radiation energy, focal spot size and intensity. X-ray optics 506 are provided to condition the primary X-ray beam 504 to a conditioned, or incident, beam 508 with the required wavelength, beam focus size, beam profile and divergence. A goniometer and sample holder 510 is used to establish and manipulate geometric relationships between the incident X-ray beam 508, the crystal sample 512 and the X-ray detector 514. The incident X-ray beam 508 strikes the crystal sample 512 and produces scattered X-rays 516 which are recorded in the detector 514. The detector 514 may be constructed as a spherical polygon as described above with the sample 512 located at the center or origin of the sphere.

The system may further include a sample alignment and monitor assembly that comprises a sample illuminator 518, typically a laser, which illuminates the sample 512 and a sample monitor 520, typically a video camera, which generates a video image of the sample to assist users in positioning the sample in the instrument center and monitoring the sample state and position.

Figure 6:
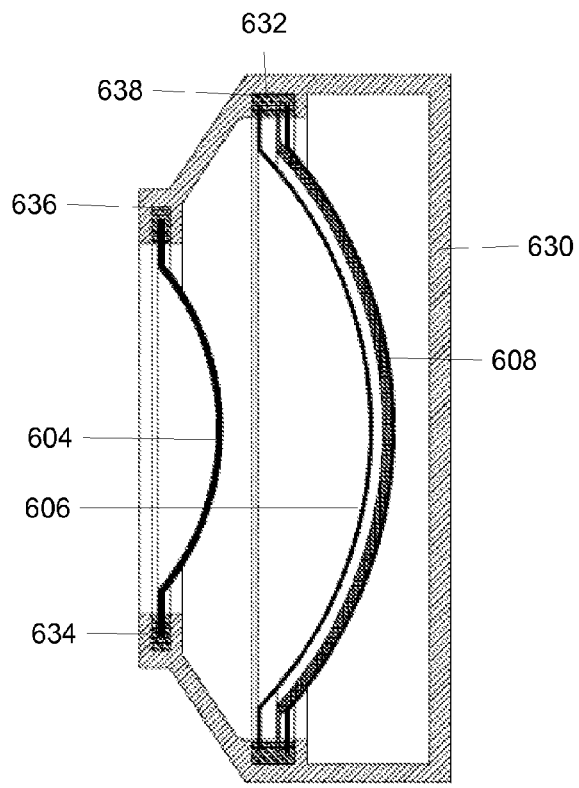
FIG. 6 is a cross-sectional view of an exemplary embodiment of the inventive detector showing mechanical construction details.

FIG. 6 is a cross-section through the center of an illustrative embodiment of the inventive detector showing mechanical construction details. As with FIG. 3, elements that correspond to those in FIGS. 2 and 3 have been given corresponding numeral designations. For example, entrance window 604 in FIG. 6 corresponds to entrance windows 204 and 304 in FIGS. 2 and 3, respectively. The detector elements are mounted in a metal housing 630 which has circular recesses 632 and 634 that hold the various components. For example, recess 634 holds the entrance window 604. The entrance window 604 is mounted in recess 634 with an insulating material 636, which may, for example, be an epoxy compound. Similarly, the grid 606 and the readout structure are mounted in recess 632 by means of insulating material 638. The entire housing 630 is filled with a working gas mixture as discussed above.

While the invention has been shown and described with reference to a number of embodiments thereof, it will be recognized by those skilled in the art that various changes in form and detail may be made herein without departing from the spirit and scope of the invention as defined by the appended claims.

What is claimed is:

1. A detector for ionizing radiation, the detector comprising:
   a housing having a cathode fabricated in a spherical polygonal shape with a radius from a material substantially transparent to the radiation and containing a working gas;
   a grid in a shape of a spherical polygon concentric with the cathode with a radius larger than the cathode radius and located within the housing;
   a resistive anode in a shape of a spherical polygon concentric with the cathode with a radius larger than the grid radius, located within the housing and mounted on a first side of an insulating substrate having a shape of a spherical polygon;
   a readout apparatus mounted on a second side of the insulating substrate opposite to the first side; and
   a voltage source for applying a first electric potential between the cathode and the grid and for applying a second electric potential between the grid and the anode, the second electric potential having sufficient amplitude to generate avalanche electrons that impinge on the anode to form charged areas.

2. The detector of claim 1 wherein the cathode, the grid and the anode are lunes.

3. The detector of claim 2 wherein the spherical angle of each lune is between $\pi$ and $2\pi$.

4. The detector of claim 1 wherein the region between the grid and the anode comprises a gas electron avalanche multiplication region in which a primary electron resulting from the radiation induces an avalanche multiplication to create an electron cloud incident upon the anode and wherein the readout apparatus is capacitively coupled to the anode, and identifies locations of charge induced on the readout apparatus by interaction of the electron cloud with the anode.

5. The detector of claim 1 wherein the ionizing radiation is produced by a sample and the sample is located at the center of the cathode, grid and anode spherical polygons.

6. An X-ray diffraction apparatus comprising:
   an X-ray source for generating a beam of X-ray radiation;
   a sample holder for holding a sample on which the beam is incident;
   a detector for detecting X-ray radiation scattered from the sample, the detector having:
      a housing having a cathode fabricated in a spherical polygonal shape with a radius from a material substantially transparent to the scattered X-ray radiation and containing a working gas;
      a grid in a shape of a spherical polygon concentric with the cathode with a radius larger than the cathode radius and located within the housing;
      a resistive anode in a shape of a spherical polygon concentric with the cathode with a radius larger than the grid radius, located within the housing and mounted on a first side of an insulating substrate having a shape of a spherical polygon;
      a readout apparatus mounted on a second side of the insulating substrate opposite to the first side; and
      a voltage source for applying a first electric potential between the cathode and the grid and for applying a second electric potential between the grid and the anode, the second electric potential having sufficient amplitude to generate avalanche electrons that impinge on the anode to form charged areas.

7. The X-ray diffraction apparatus of claim 6 wherein the cathode, the grid and the anode are lunes.

8. The X-ray diffraction apparatus of claim 7 wherein the spherical angle of each lune is between $\pi$ and $2\pi$.

9. The X-ray diffraction apparatus of claim 6 wherein the region between the grid and the anode comprises a gas electron avalanche multiplication region in which a primary electron resulting from the X-ray radiation induces an avalanche multiplication to create an electron cloud incident upon the anode and wherein the readout apparatus is capacitively coupled to the anode, and identifies locations of charge induced on the readout apparatus by interaction of the electron cloud with the anode.

10. The X-ray diffraction apparatus of claim 6 wherein the X-ray radiation is produced by a sample and the sample is located at the center of the cathode, grid and anode spherical polygons.

* * * * *